US010299801B2

(12) United States Patent
Grant et al.

(10) Patent No.: US 10,299,801 B2
(45) Date of Patent: May 28, 2019

(54) DISTAL FEMORAL JIG ASSEMBLY

(71) Applicant: DEPUY IRELAND UNLIMITED COMPANY, Cork (IE)

(72) Inventors: Stuart Grant, Bexley (GB); Xiaohui Dong, Jiangsu (CN)

(73) Assignee: DEPUY IRELAND UNLIMITED COMPANY, Cork (IE)

( * ) Notice: Subject to any disclaimer, the term of this patent is extended or adjusted under 35 U.S.C. 154(b) by 895 days.

(21) Appl. No.: 14/777,953

(22) PCT Filed: Apr. 11, 2014

(86) PCT No.: PCT/EP2014/057404
§ 371 (c)(1),
(2) Date: Sep. 17, 2015

(87) PCT Pub. No.: WO2014/167104
PCT Pub. Date: Oct. 16, 2014

(65) Prior Publication Data
US 2016/0128702 A1    May 12, 2016

(30) Foreign Application Priority Data

Apr. 12, 2013  (CN) .......................... 2013 1 0140826

(51) Int. Cl.
*A61B 17/15* (2006.01)
*A61B 17/14* (2006.01)
*A61B 17/00* (2006.01)

(52) U.S. Cl.
CPC ............ *A61B 17/155* (2013.01); *A61B 17/14* (2013.01); *A61B 2017/0046* (2013.01)

(58) Field of Classification Search
CPC ..... A61B 17/15; A61B 17/151; A61B 17/154; A61B 17/155
See application file for complete search history.

(56) References Cited

U.S. PATENT DOCUMENTS 1,440,072 A    12/1922  Greener
4,453,539 A     6/1984  Raftopoulos
(Continued)

FOREIGN PATENT DOCUMENTS

EP       687448 A1    12/1995
EP      0791334 A1     8/1997
(Continued)

OTHER PUBLICATIONS

Translation of Japanese Office Action for Corresponding Japanese Patent Application 2016-506991, dated Feb. 19, 2018, 5 pages.
(Continued)

*Primary Examiner* — Eric S Gibson

(57) ABSTRACT

A cutting apparatus for resecting a distal face of a femur prior to implanting a femoral component of a total knee prosthesis, comprises an elongate rod adapted for inserting into an intramedullary canal of the femur, a distal femoral cutting block, and a distal femoral jig assembly. The jig assembly can position the distal femoral cutting block on either left leg or right leg. It includes a distal femoral jig having at least one passage for slidingly receiving the rod with a preset valgus angle and a distal end face being adapted for abutting against on the distal face of the femur of either left leg or right leg dependent on its two flip orientations.

15 Claims, 9 Drawing Sheets

(56) References Cited

U.S. PATENT DOCUMENTS

| | | | |
|---|---|---|---|
| 4,474,177 A | 10/1984 | Whiteside | |
| 4,646,729 A | 3/1987 | Kenna et al. | |
| 4,703,751 A | 11/1987 | Pohl | |
| 4,759,350 A * | 7/1988 | Dunn | A61B 17/154 606/82 |
| 5,037,423 A | 8/1991 | Kenna | |
| 5,116,335 A | 5/1992 | Hannon | |
| 5,364,401 A | 11/1994 | Ferrante | |
| 5,454,816 A | 10/1995 | Ashby | |
| 5,484,446 A * | 1/1996 | Burke | A61B 17/154 606/86 R |
| 5,514,140 A | 5/1996 | Lackey | |
| 5,562,674 A | 10/1996 | Stalcup | |
| 5,624,444 A | 4/1997 | Wixon | |
| 5,628,749 A | 5/1997 | Vendrely | |
| 5,662,656 A | 9/1997 | White | |
| 5,676,668 A * | 10/1997 | McCue | A61B 17/155 606/102 |
| 5,683,397 A | 11/1997 | Vendrely et al. | |
| 5,688,279 A | 11/1997 | McNulty | |
| 5,693,048 A | 12/1997 | Stalcup | |
| 5,720,752 A | 2/1998 | Elliott | |
| 5,830,216 A | 11/1998 | Insall | |
| 5,910,143 A | 6/1999 | Cripe | |
| 6,013,081 A * | 1/2000 | Burkinshaw | A61B 17/155 606/102 |
| 6,077,270 A | 6/2000 | Katz | |
| 6,193,723 B1 | 2/2001 | Cripe | |
| 6,558,391 B2 | 5/2003 | Axelson, Jr. | |
| 6,613,052 B1 | 9/2003 | Kinnett | |
| 6,740,092 B2 | 5/2004 | Lombardo | |
| 6,916,325 B2 * | 7/2005 | Kana | A61F 2/4657 606/89 |
| 6,979,299 B2 | 12/2005 | Peabody | |
| 7,374,563 B2 * | 5/2008 | Roger | A61B 17/155 606/88 |
| 7,628,793 B2 | 12/2009 | Calton | |
| 7,794,467 B2 | 9/2010 | McGinley | |
| 7,959,637 B2 * | 6/2011 | Fox | A61B 17/1764 606/88 |
| D651,318 S | 12/2011 | Cronin | |
| 8,152,807 B2 | 4/2012 | Edwards | |
| 8,287,541 B2 | 10/2012 | Nelson | |
| 8,979,847 B2 * | 3/2015 | Belcher | A61B 17/155 606/79 |
| 9,101,443 B2 | 8/2015 | Bonutti | |
| 9,204,884 B2 | 12/2015 | Jordan | |
| 9,314,282 B2 * | 4/2016 | Kecman | A61B 17/7266 |
| 9,572,590 B2 | 2/2017 | Singhal et al. | |
| 9,655,632 B2 * | 5/2017 | Dmuschewsky | A61B 17/155 |
| 2002/0198531 A1 | 12/2002 | Millard | |
| 2004/0153084 A1 | 8/2004 | Haney | |
| 2006/0015113 A1 | 1/2006 | Masini | |
| 2006/0036248 A1 | 2/2006 | Ferrante | |
| 2006/0200163 A1 * | 9/2006 | Roger | A61B 17/155 606/89 |
| 2007/0213738 A1 | 9/2007 | Martin | |
| 2008/0097451 A1 | 4/2008 | Chen | |
| 2008/0177337 A1 | 7/2008 | McGovern | |
| 2009/0043310 A1 | 2/2009 | Rasmussen | |
| 2009/0125114 A1 | 5/2009 | May | |
| 2009/0149964 A1 | 6/2009 | May | |
| 2009/0204115 A1 | 8/2009 | Dees, Jr. | |
| 2010/0010493 A1 * | 1/2010 | Dower | A61B 17/157 606/87 |
| 2010/0057088 A1 | 3/2010 | Shah | |
| 2010/0121334 A1 * | 5/2010 | Couture | A61B 17/155 606/87 |
| 2010/0234850 A1 | 9/2010 | Dees, Jr. | |
| 2010/0241126 A1 * | 9/2010 | Ghijselings | A61B 17/025 606/88 |
| 2010/0292694 A1 * | 11/2010 | Kecman | A61B 17/155 606/62 |
| 2011/0009868 A1 | 1/2011 | Sato | |
| 2012/0136359 A1 | 5/2012 | Grunder | |
| 2013/0317501 A1 | 11/2013 | Booth | |
| 2013/0331844 A1 | 12/2013 | Booth | |
| 2013/0338671 A1 | 12/2013 | Beedall | |
| 2014/0324054 A1 * | 10/2014 | Dmuschewsky | A61B 17/155 606/89 |
| 2016/0128702 A1 * | 5/2016 | Grant | A61B 17/155 606/82 |
| 2017/0100132 A1 * | 4/2017 | Collazo | A61B 17/15 |

FOREIGN PATENT DOCUMENTS

| | | |
|---|---|---|
| EP | 689796 A1 | 1/2002 |
| EP | 1574177 A1 | 9/2005 |
| EP | 1444957 B1 | 3/2007 |
| FR | 2752519 A1 | 2/1998 |
| FR | 2943528 A1 | 10/2010 |
| JP | 9-75366 A | 3/1997 |
| WO | WO 9618351 A1 | 6/1996 |
| WO | WO 97/21390 A1 | 6/1997 |
| WO | WO 02058575 A1 | 8/2002 |
| WO | WO 06090361 A3 | 8/2006 |
| WO | WO 09006741 A1 | 1/2009 |
| WO | WO 09037471 A3 | 6/2009 |
| WO | WO 12/066305 A1 | 5/2012 |
| WO | WO 12066305 A1 | 5/2012 |
| WO | WO 14/167104 | 10/2014 |

OTHER PUBLICATIONS

International Search Report for Application No. PCT/EP2014/057404, dated Jun. 27, 2014 (4 pages).

Labourdette, P.; Femoral-Patellar Prosthesis and Ancillary Device for Making a Trochlear Impression for Receiving Said Prosthesis—European Pub. No. EP687448A1; Dec. 20, 1995; English Abstract; Micropatent Report; 2010 Micropatent LLC.

\* cited by examiner

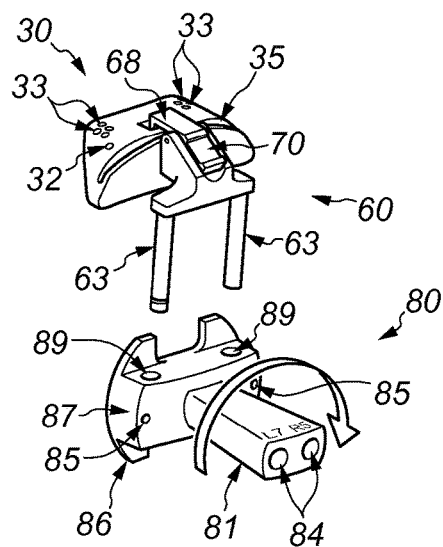
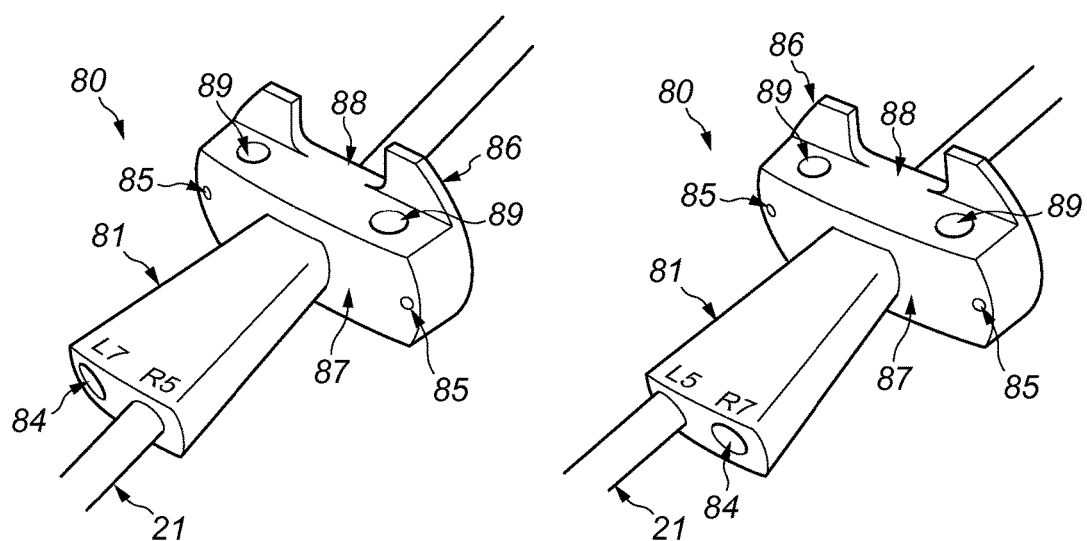
Fig. 6
Fig. 7A    Fig. 7B

DISTAL FEMORAL JIG ASSEMBLY

CROSS REFERENCE TO RELATED APPLICATION

This application is a National Stage 35 U.S.C. 371 of International Patent Application PCT/EP2014/057404 filed Apr. 11, 2014, claiming priority to Chinese application 201310140826.3, filed Apr. 12, 2013.

BACKGROUND OF THE INVENTION

The invention relates to a distal femoral cutting apparatus for resecting a distal face of a femur at a preset valgus angle relative to a patient's intramedullary canal prior to implanting the femoral component of a total knee prosthesis.

The invention also relates to a distal femoral jig assembly used for the mentioned distal femoral cutting apparatus.

Knee joint is the biggest and most complicated joint in a human body. Total knee replacement (TKR) is adopted for severely damaged knee joint. As the knee replacement becomes the most popular surgery for severe knee injuries, research related to TKR are attracting more and more attention.

TKR surgery involves implantation of articulating femoral and tibial components to distal femur and proximal tibia, respectively. Since a femur projects distally in an inward manner at a valgus angle relative to the anatomic axis of the human body and a distal face of the femur has a fossa intercondylaris and is not a planar face, the femur must be resected to conform to the size and shape of the respective prosthetic component so as to properly affix to the prosthetic component. The term "valgus angle" means the angle between the axis of the main body and the channel being considered. In the case of the femur, the valgus angle is the angle formed between the anatomic axis of the patient and the longitudinal axis of the femur, and in the case of the jig, the valgus angle means the angle between the axis of the jig and the passages in the jig.

A plurality of instruments and/or jigs for resecting the distal femur have been developed. Many of the instruments include a cutting block that references an intramedullary rod inserted in the intramedullary canal of the femur. However, such instruments usually cannot provide easily adjustable jig assembly to accommodate to different patients. Meanwhile, due to the distal femur has an asymmetrical shape, the design of the instruments for TKR surgery has to take that into consideration and thereby resulting in complicated structures.

US-A-2010/0057088 relates to a distal femoral cutting apparatus which can be used for resecting either the left or right femur. The apparatus has a handle 12, a sword 14, a base cartridge 26 and a face plate 28 connected by mating threaded connectors so that the various parts can be interchanged with similar parts having different physical properties such as angular orientation. In other words, if the surgeon wants to adjust the valgus angle of the apparatus relative to the anatomic axis of the patient, he or she has to change the corresponding parts of the apparatus on the site. For a surgical procedure, it is rather cumbersome.

BRIEF SUMMARY OF THE INVENTION

It would be desirable to provide a distal femoral cutting apparatus which can be used for resecting either the left or right femur with easily adjustable valgus angles.

The present invention also provides a distal femoral jig assembly having a flip feature and suitable for use for the mentioned distal femoral cutting apparatus.

The present invention also provides a distal femoral cutting apparatus which can be used for resecting either left or right femur with a distal femoral jig assembly having a flip feature. Such flip feature allows the distal femoral cutting apparatus to resect one of the left and right femurs at the first flip orientation and to resect the other one of the left and right femurs at a second flip orientation by a simple flipping action.

The invention also provides a distal femoral jig assembly is used with a cutting apparatus for resecting a distal face of a femur prior to implanting a femoral component of a total knee prosthesis, the cutting apparatus comprising a rod adapted for inserting into an intramedullary canal of the femur, and a distal femoral cutting block configured for guiding resection of the distal face of the femur, in which the distal femoral jig assembly is capable of positioning the distal femoral cutting block on either left leg or right leg and comprising a distal femoral jig, the distal femoral jig comprising at least one passage for slidingly receiving the rod with a preset valgus angle and a distal end face being adapted for abutting against on the distal face of the femur of either left leg or right leg dependent on its two flip orientations: in a first flip orientation the rod can be inserted in a selected one of the at least one passage having the preset valgus angle for one of the left and right legs, and in a second flip orientation after the distal femoral jig being flipped over about 180° about a jig longitudinal axis the rod can be inserted in a selected one of the at least one passage having the preset valgus angle for the other one of the left and right legs The invention therefore provides cutting apparatus for resecting a distal face of a femur prior to implanting a femoral component of a total knee prosthesis, comprising:
  (a) an elongate rod adapted for inserting into an intramedullary canal of the femur,
  (b) a distal femoral cutting block configured for guiding resection of the distal face of the femur,
  (c) a distal femoral jig assembly capable of positioning the distal femoral cutting block on either left leg or right leg and comprising a distal femoral jig, the distal femoral jig comprising at least one passage for slidingly receiving the rod with a preset valgus angle and a distal end face being adapted for abutting against on the distal face of the femur of either left leg or right leg dependent on its two flip orientations: in a first flip orientation the rod can be inserted in a selected one of the at least one passage having the preset valgus angle for one of the left and right legs, and in a second flip orientation after the distal femoral jig being flipped over about 180° about a jig longitudinal axis the rod can be inserted in a selected one of the at least one passage having the preset valgus angle for the other one of the left and right legs.

The distal femoral cutting apparatus of the present invention has a reduced number of components, can reduce cost and improve cleanability and sterilisation.

The distal femoral jig assembly according to the present invention can be used for resecting either left or right femur with the simplified flip feature which has different preset valgus angles and can dramatically simplify the operation procedure.

BRIEF DESCRIPTION OF THE DRAWINGS

Embodiments of the invention are described below by way of example with reference to the accompanying drawings, in which:

FIG. 6 is an exploded view showing the distal femoral cutting block and the distal femoral jig outrigger assembled together and a distal femoral jig being taken a flipping action.

FIG. 7A is a view showing the first flip orientation of the distal femoral jig and FIG. 7B is a view showing a second flip orientation of the distal femoral jig after being taken the flipping action as shown in FIG. 6.

DETAILED DESCRIPTION OF THE INVENTION

Figure 1:
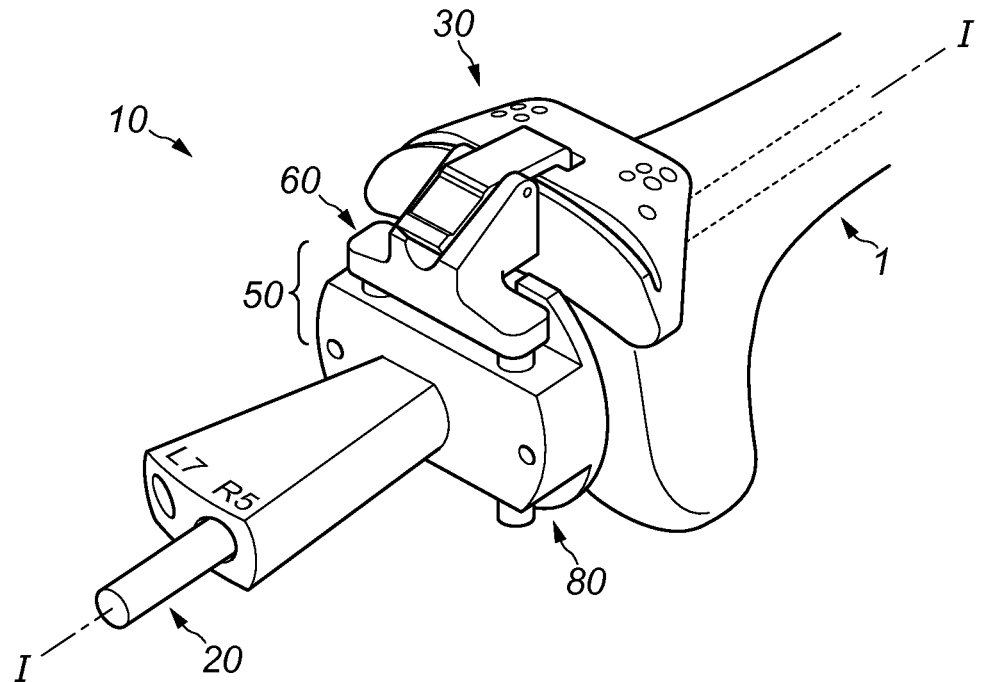
FIG. 1 is a perspective view of distal femoral cutting apparatus in one of valgus angles in a first flip orientation.

Unless otherwise defined, all technical and scientific terms used herein in their various grammatical forms have the same meaning as commonly understood by the skilled reader. The terms anterior, posterior, proximal, distal, medial, lateral, sagital, coronal, and transverse are used herein with their conventional medical/anatomical meaning. When used in connection with the distal femoral cutting apparatus, the terms proximal and distal reference the surgeon using the apparatus. In contrast, when used in connection with the femur with which the distal femoral cutting apparatus is used, the terms proximal, distal, anterior and posterior reference the patient. As mentioned above, the term "valgus angle" means the angle between the axis of the main body and the channel being considered. In the case of the femur, the valgus angle is the angle formed between the anatomic axis of the patient and the longitudinal axis of the femur, and in the case of the jig, the valgus angle means the angle between the axis of the jig and the passages in the jig.

FIGS. 1 to 15 show distal femoral cutting apparatuses. The distal femoral cutting apparatus is designated generally by reference numeral 10 and can guide a saw blade during resection of a distal face of a femur at an angle relative to the patient's intramedullary canal prior to implanting a femoral component of a total knee prosthesis. In particular, the distal femoral cutting apparatus 10 can be used for resecting either the left or right femur with preset valgus angles. The structure and operation of the cutting apparatus 10 will be described in detail as below.

Figure 2A:
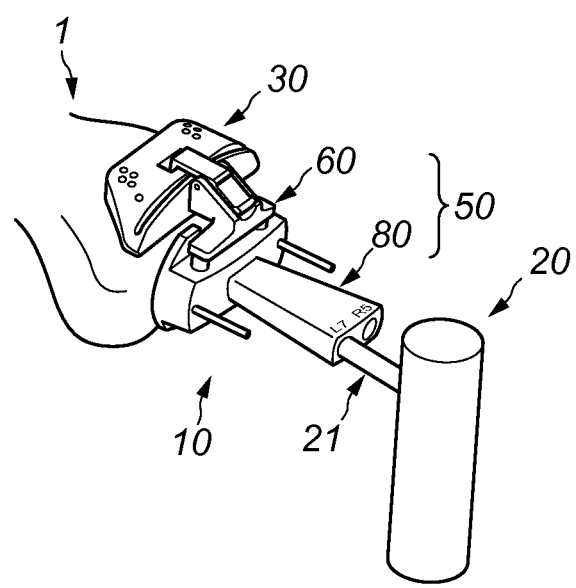
FIG. 2A is another perspective view of the distal femoral cutting apparatus in accordance in another valgus angle in the first flip orientation.

FIGS. 1 and 2A show in different visual angles the cutting apparatus 10 attached to the distal femur 1 of the patient in different preset valgus angles in a first flip orientation. The cutting apparatus 10 comprises a rod assembly 20 having a longitudinal axis I-I and adapted for inserting into the intramedullary canal of the femur, a distal femoral cutting block 30 configured for guiding a saw blade to resect the femur, and a distal femoral jig assembly 50 capable of appropriately positioning the distal femoral cutting block 30 on either left leg or right leg with different preset valgus angles via the rod assembly 20. The distal femoral jig assembly 50 comprises a distal femoral jig 80 capable of sliding on a rod 21 of the rod assembly 20 and abutting against a distal face of the femur. The distal femoral jig assembly 50 further comprises a distal femoral jig outrigger 60 having at least one leg for inserting into corresponding at least one hole of the distal femoral jig 80 and a clip 64 for engaging with the distal femoral cutting block 30 to position it. The distal femoral jig 80 has at least one passage for receiving the rod 21 with different valgus angles and can be adapted for left leg and right leg with a "flip" feature having a first flip orientation and a second flip orientation, in the first flip orientation, the rod 21 can be inserted in a selected one of the at least one passage having a preset valgus angle for one of the left and right legs, and in a second flip orientation by flipping over the distal femoral jig 80 about 180° about its axis from the first flip orientation, the rod 21 can be inserted similarly alternatively in a selected one of the at least one passage having a preset valgus angle for the other one of the left and right legs.

Figure 2B:
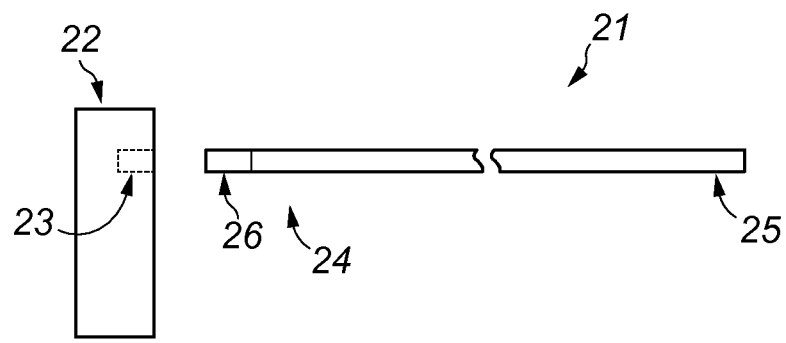
FIG. 2B is a side view of a rod assembly of the distal femoral cutting apparatus.
Figure 2C:
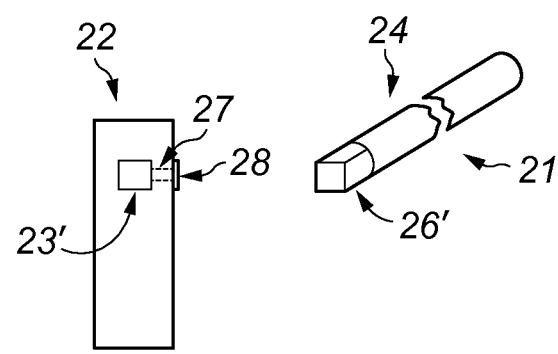
FIG. 2C is view of another rod assembly of the apparatus.

The rod assembly 20 comprises the elongate rod 21 extending along the longitudinal axis I-I and used for inserting into the medullary canal of the femur. The rod assembly 20 also comprises a handle 22 for removeably attaching to the rod 21. As shown in FIGS. 2A and 2B, the elongate rod 21 has a proximal end 24 and a distal end 25, and the handle 22 has a blind hole 23. The proximal end 24 has a section 26 formed with external screw thread and the blind hole 23 is formed with internal screw thread for mating with the screwed section 26 of the proximal end 24 of the rod 21. Other arrangements can be used to connect the rod 21 to the handle 22 releasably. For example, as shown in FIG. 2C, the proximal end 24 may have a squared section 26', and the handle 22 has a squared blind hole 23' for receiving the squared section 26' and a traverse hole 27 communicating with the squared blind hole 23' for receiving a pin 28. When the squared section 26' of the rod 21 is inserted into the squared blind hold 23', the pin 28 may be inserted into the pin hole 27 and abut against a side of the squared section 26' to prevent it from moving. Of course, the shape of the blind hole of the handle 22 is not limited to the square shape. It may be in a polygonal shape and the proximal end 24 has a corresponding shaped section for mating with the blind hole.

Other arrangements can be used to connect the handle 22 to the rod 21. In addition, the rod 21 and the handle 22 may be formed integrally.

Figure 3A:
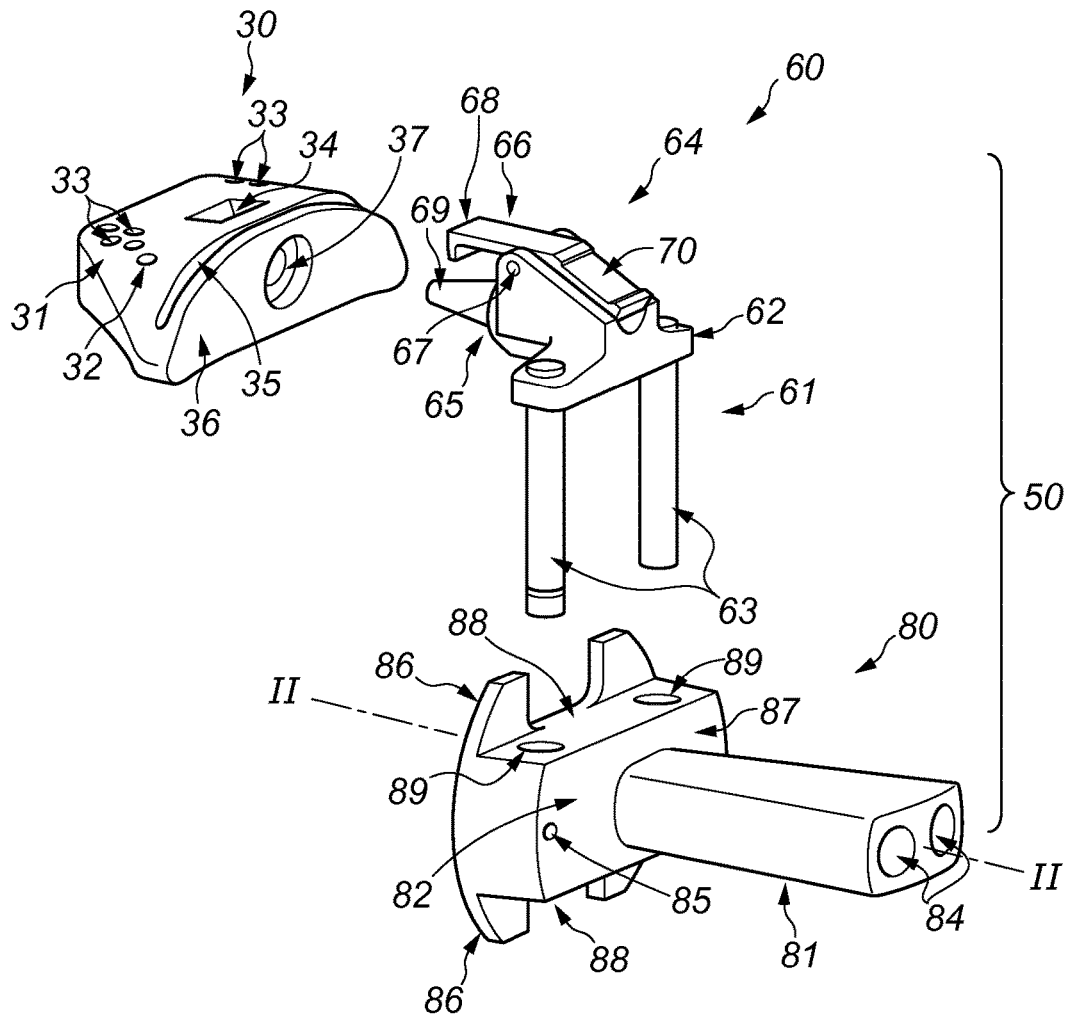
FIG. 3A is an exploded view showing a distal femoral cutting block and a distal femoral jig assembly of the distal femoral cutting apparatus of FIGS. 1 and 2.

FIG. 3A shows the distal femoral cutting block 30 which comprises a main body 31. The main body 31 is left-and-right symmetrical and has a front surface 41, a vertical rear surface 36, an upper surface 40, a lower surface 42 and two side surfaces (see FIGS. 3A and 4). The lower surface 42 has a curved lower surface portion 38 generally conforming to the human anatomy of the anterior distal femur and a substantially flat lower surface portion 39 (best shown in FIGS. 4, 5A and 5B). With such a curved lower surface portion 38, when being positioned on the distal femur of the patient, the distal femoral cutting block 30 may be positioned more stably. Preferably, the upper surface 40 is also a curved surface for avoiding any injury to the patient or the surgeon. The main body of the distal femoral cutting block may instead have other shaped surfaces, such as completely flat lower and/or upper surfaces, or stepped lower and/or upper surfaces, or inclined lower and/or upper surfaces. In addition, as shown in FIGS. 1, 2A and 3A, the main body 31 has a smaller front end and a bigger rear end so that the surgeon may manipulate the cutting block conveniently. However, the shape of the cutting block is not limited to the illustrated one, and other shapes for the main body may be used.

As shown in FIGS. 2A and 3A, the main body 31 has several groups of through holes passing through the main body from the upper surface 40 to the lower surface portion 38. The through holes of the first group are convergent (or angled) holes 32 for receiving pins (such as pins sold under the trade mark SP2 by Ethicon Endo-Surgery Inc.) to fix the distal femoral cutting block 30 to the anterior femur. The through holes of the second group are reposition holes 33 for receiving pins (such as Steinmann pins) which allow the distal femoral cutting block 30 to be adjustable.

As shown in the embodiment of FIG. 2A, there are two convergent holes 32 which are arranged left-and-right symmetrically. Of course, the number of the convergent holes may be increased or reduced as desired, and they can be symmetrical or unsymmetrical as long as they can fix the distal femoral cutting block 30 to the anterior femur. Furthermore, the convergent holes can be omitted since appropriate arranged reposition holes can also fulfill the function of fixation.

Figure 4:
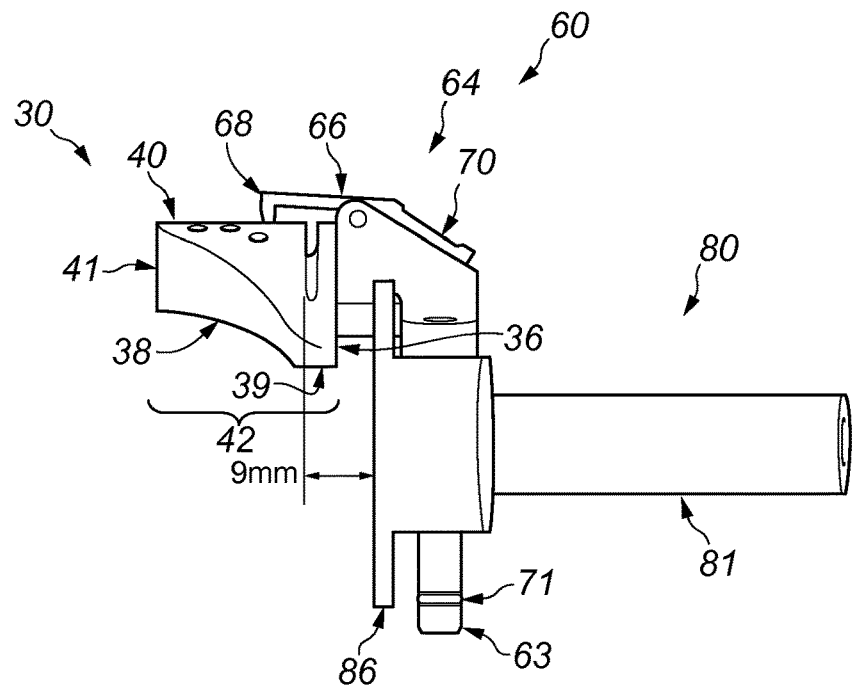
FIG. 4 is a side view of the distal femoral cutting block and the distal femoral jig assembly assembled together.
Figure 11:
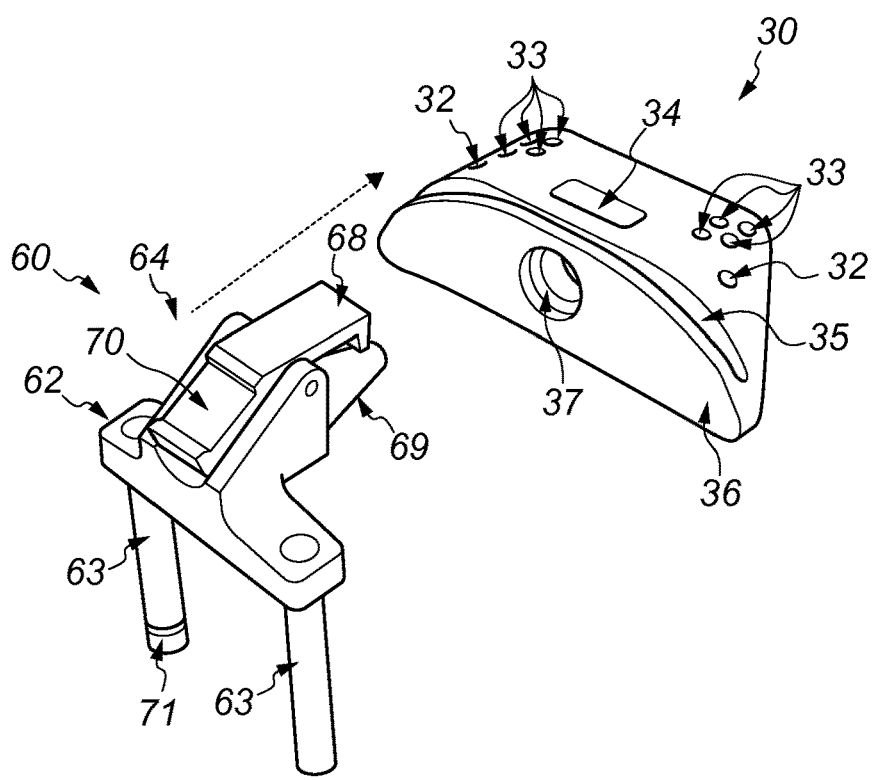
FIG. 11 is a view showing assembling of the distal femoral jig outrigger to the distal femoral cutting block.
Figure 12:
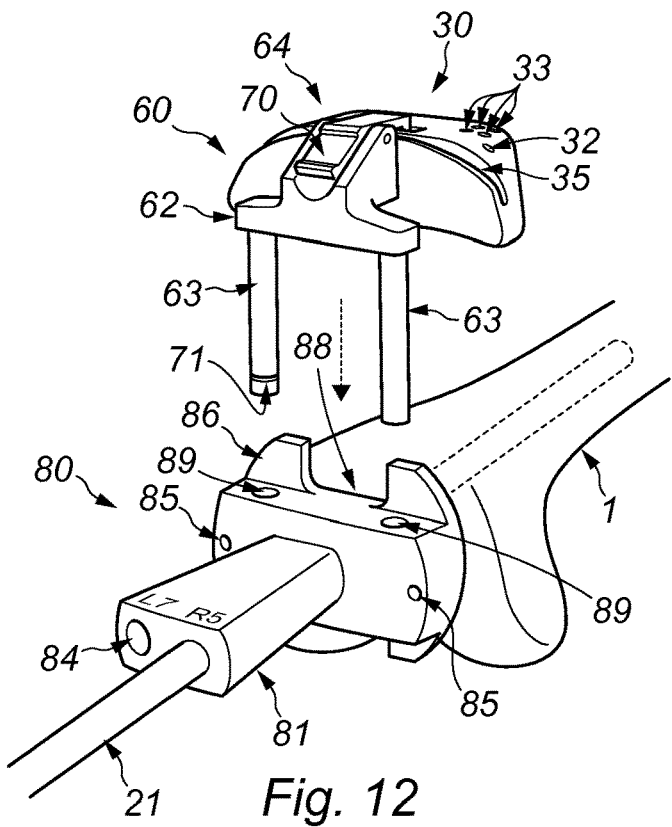
FIG. 12 is a view showing assembling of the assembled distal femoral jig outrigger and the distal femoral cutting block to the distal femoral jig abutting against the distal face of the distal femur of FIG. 10.

In the constructions shown in FIGS. 2 and 11, there are totally eight reposition holes 33 with four reposition holes 33 on the left side of the upper surface 40 and four reposition holes 33 on the right side of the upper surface 40 which allow the distal femoral cutting block 30 to be adjustable. As can be seen in FIG. 11, the arrangement of the four reposition holes 33 on the left side of the upper surface 40 is the same as that on the right side of the upper surface 40. Specifically, the four reposition holes 33 on either side are arranged in two longitudinal lines and staggered with each other. In the shown example, the first reposition hole on the left line is taken as a reference and marked as "0" position. As shown in FIG. 4, when assembled together, a distance between a distal end surface of the distal femoral jig 80 and a distal wall forming a cutting slot 35 in the distal femoral cutting block 30 is 9 mm and inserting two pins into the "0" position reposition holes will fix the resecting depth as 9 mm, which is used as a basic or reference resecting depth. The other repositions holes 33 allow the distal femoral cutting block 30 to be adjustable from 9 mm (see FIG. 4) by +4 mm, +2 mm, −2 mm so that the resecting depths are adjusted correspondingly as 13 mm, 11 mm and 7 mm for different patients. The number of the reposition holes may be increased or reduced and other arrangement of the reposition holes may be adopted for flexibly adjusting the resecting depth as desired.

A central hole 34 is provided on a central portion of the upper surface 40 of the cutting block 30 for receiving a tip end 68 of the clip 64 of the distal femoral jig assembly 50. On a central portion of the vertical rear surface 36 of the cutting block 30, there is a big central opening 37 for receiving a trunion 69 of the distal femoral jig assembly 50. The central axes of the central hole 34 and the central opening 37 may be or may not be in a perpendicular position relationship, and the hole 34 and the opening 37 may be or may not communicate with each other. As shown in FIG. 3A, the central hole 34 is in a rectangular shape. However, it is not necessary for the central hole 34 to be a rectangular hole, other shapes such as a semi-circular shape may be suitable as long as the central hole 34 can receive the tip end 68. As can be seen from FIG. 3A, the central opening 37 is a tapered counterbore. The stepped portion of the central opening 37 can prevent the trunion 69 from moving further into the opening 37. The shape of the central opening 37 is not limited to the shape shown in the drawings, and other shapes (such as cylindrical counter-bore, cylindrical or tapered hole with protrusions or a shoulder protruding from the inner wall of the hole, and the like) are also suitable for receiving the trunion 69 and preventing it from further moving.

The cutting slot 35 is formed in a proximal portion of the main body 31 and parallel with the vertical rear surface 36 of the main body 31. As shown in FIG. 3A, the cutting slot 35 is a through slot which allow a saw blade to pass through so as to cut off a portion of the distal femur. Although only one cutting slot 35 is shown in the drawings, there may be a plurality of cutting slots for selectively cutting off different lengths of the distal femur. Moreover, the vertical rear surface 36 or say the proximal end face of the cutting block 30 may be used as a reference for resection. In the example shown in FIG. 4, the resection initiated from the proximal end face of the cutting block 30 will resect 4 mm less distal femur than the resection initiated from the cutting slot. In addition, the plurality of cutting slots may be used alone or in combination with the reposition holes for adjusting the resecting depths. When the cutting slots are used alone for adjusting resecting depths, the reposition holes may be omitted.

Figure 3B:
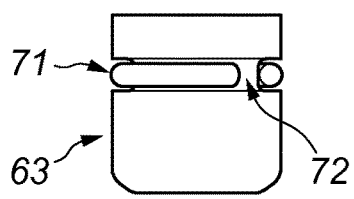
FIG. 3B is an enlarged view showing a part of a distal femoral jig outrigger of the distal femoral jig assembly shown in FIG. 3A.

In the construction shown in FIGS. 2A and 3A, the distal femoral jig assembly 50 comprises the distal femoral jig outrigger 60 and the distal femoral jig 80 supporting the distal femoral jig outrigger 60. The distal femoral jig outrigger 60 includes a support 61 and the clip 64 supporting by the support 61. The support 61 comprises a beam 62 and at least one leg extending vertically and downwardly from the beam 62 for a quick connection with the distal femoral jig 80. In the exemplified embodiment shown in FIG. 3A, the support 61 has two legs 63 extending from the beam 62 vertically and downwardly so that the support 61 is in an inverted U shape (or generally U shape). The clip 64 includes a base portion 65 formed integrally with the beam 62 and a movable portion 66 capable of pivoting around a pivot pin 67 passing through the pinhole in the base portion 65 via a spring (not shown in the figures). The base portion 65 has the trunion 69 at its front end for insertion into the central opening 37 and two side walls protruding from the beam 62 for protecting the spring. In the example shown in FIG. 3A, the trunion 69 has a substantially cylindrical portion and a truncated cone portion having a biggest diameter smaller than the diameter of the cylindrical portion. The truncated cone portion of the trunion 69 is used for easy insertion into the central opening 37. When the trunion 69 is inserted into the central opening 37 of the distal femoral cutting block 30, the end face of the cylindrical portion abuts against the stepped portion of the central opening 37 for preventing further movement. The trunnion 69 and the central opening 37 fit the jig outrigger 60 with the cutting block 30, and their shapes may be changed within the spirit of the present invention. For example, when the central opening 37 is a cylindrical counter-bore or a cylindrical hole with protrusions or a shoulder as mentioned above, the trunion 69 may correspondingly have a bigger diameter cylindrical portion and a smaller diameter cylindrical portion. The movable portion 66 has a proximal portion used as a button 70 and a distal portion having the hook-like tip end 68. When assembled with the distal femoral cutting block 30, the trunnion 69 is inserted into the central opening 37, and the tip end 68 bites into the central hole 34. Of course, the tip end 68 may have other shapes as long as it can bite into the central hole 34 for a quick connection. At least one of the legs 63 has a groove 72 formed circumferentially around its lower end (see FIGS. 3A and 3B). As best shown in FIG. 3B, a C-clip 71 is arranged in the groove 72. When the two legs 63 are inserted into the distal femoral jig 80, the C-clip(s) 71 can provide friction to prevent the distal femoral jig outrigger 60 from sliding off the jig 80, as described below.

FIGS. 3A, 7A and 7B show the distal femoral jig 80 in detail. In particular, FIG. 7A and FIG. 7B are views respectively showing the first flip orientation and the second flip orientation of the distal femoral jig 80. In the device shown in the drawings, the distal femoral jig 80 has a longitudinal axis II-II (as shown in 3A) and comprises a guiding bar 81 extending along the longitudinal axis II-II for guiding the rod 21, a positioning block 82 formed integrally at a distal end of the guiding bar 81 for a quick connection with the jig outrigger 60 and abutting against the end face of the distal femur, and at least one passage 84 extending through the jig 80, i.e., the guiding bar 81 and the positioning block 82, with a preset valgus angle towards the femur for slideably receiving the rod 21 so as to position the cutting block 30 with the preset valgus angle. The positioning block 82 may be formed separately and then attached to the distal end of the guiding bar 81 by known means. The positioning block 82 is formed with a vertical distal end face perpendicular to the longitudinal axis II-II for stably abutting against the end face of the distal femur. The positioning block 82 is also formed with at least one vertical through hole 89 for receiving the at least one leg 63 of the distal femoral jig outrigger 60. Due to the at least one vertical through hole 89, directly flipping over the distal femoral jig 80 can still allow the at least one leg 63 to be inserted through the at least one vertical through hole 89 so as to easily connect the jig outrigger 60 and the jig 80 together. Meanwhile, due to the vertical distal end face and the at least one passage 84 with the preset valgus angle, before flipping over the jig 80, i.e., in the first flip orientation, the assembled cutting apparatus can be used for resecting the distal femur of one of the left and right legs, and after flipping over the jig 80, i.e., in the second flip orientation, the assembled cutting apparatus can be used for resecting the distal femur of the other one of the left and right legs.

As an example, two passages 84 extend throughout the distal femoral jig 80, i.e., the guiding bar 81 and the positioning block 82, towards the femur for passage of the rod 21. The two passages 84 each have a valgus angle with respect to the longitudinal axis II-II of the distal femoral jig 80. In the construction shown in the drawings, the two passages 84 extend in a convergent manner from a proximal portion to a distal portion of the distal femoral jig 80, i.e, toward the femur. In an example, though the two passages 84 are arranged in the convergent manner, they do not meet at one point but the extension lines of the central lines of the two passages meet at a point. In another example, the central lines of the two passages meet at a point on the distal face of the jig 80. The arrangement of the one, two or more passages are not limited to the convergent manner. For example, the passages may be arranged in a divergent manner. In such a divergent manner, the starting points of the two or more passages may be or may not be one and the same point.

In the construction shown in the drawings, one of the two passages 84 has a valgus angle of 5° with respect to the jig longitudinal axis II-II and the other one of the two passages 84 has a valgus angle of 7° with respect to the jig longitudinal axis II-II, such that the distal femoral jig 80 can be rotated (or say "flip") either clockwise (see FIG. 6) or counterclockwise to provide the 5 and 7 degree angles settings for each leg: for example, one side has 5° left and 7° right, the opposite side has 7° left and 5° right (as shown in FIGS. 6, 7A and 7B). The valgus angles may be different from 5° or 7°, as long as the valgus angle difference between the two passages is between 1° and 3° and the two valgus angles both are selected between 4° and 10°.

As mentioned above, at least one passage is provided in the distal femoral jig 80. If there is only one passage formed in the distal femoral jig, then the preset valgus angle for the left leg and the right leg by flipping over the distal femoral jig is the same. If there are two or more passages formed in the distal femoral jig, then the preset valgus angles for the patient can be selected as desired.

For the convenient grip of the surgeon, the guiding bar 81 may have a tapered shape or a truncated cone shape as shown in FIGS. 7A and 7B. This is not necessary. For example, it may have a funnel shape. Other shapes might be used.

As mentioned above, the positioning block 82 is used for a quick connection with the jig outrigger 60 and abutting against the end face of the distal femur. In the construction shown in FIG. 3A, the positioning block 82 comprises the vertical distal end face perpendicular to the jig longitudinal axis II-II for abutting the end face of the distal femur and two vertical through holes 89 for receiving the two legs of the jig outrigger 60. Such structure allows the jig 80 to flip over for the use of either left or right leg distal femur resection. In the specific example shown in the FIG. 3A, the positioning block 82 is a substantially cuboid having two parallel front and rear surfaces perpendicular to the jig longitudinal axis II-II and two parallel upper and lower surfaces. The two vertical through holes 89 extend from the upper surface to the lower surface of the positioning block 82 for receiving the two legs 63 of the distal femoral jig outrigger 60. When the jig outrigger 60 has at least one leg, the positioning block 82 may be correspondingly provided with at least one vertical through hole for receiving the at least one leg. Or alternatively, the positioning block 82 may be provided with vertical through holes more than the legs of the jig outrigger 60 for selectively receiving the legs of the jig outrigger 60. Although the shape of the positioning block 82 shown in the example is a substantially cuboid and symmetrical with respect to a vertical plane passing through the jig longitudinal axis II-II and with respect to a horizontal plane passing through the jig longitudinal axis II-II, the shape of positioning block 82 is not limited to the above mentioned one, it may be a regular or irregular shape, symmetrical (for example, only symmetrical with respect to the vertical plane passing through the jig longitudinal axis II-II or only symmetrical with respect to the horizontal plane passing through the jig longitudinal axis II-II) or unsymmetrical, as long as it comprises the vertical distal end face perpendicular to the jig longitudinal axis II-II for abutting the end face of the distal femur and at least one vertical through hole for receiving the at least one leg of the jig outrigger 60. As used herein, term "vertical" means it is perpendicular to the "horizontal" plane formed by the passages 84. Thus, the vertical rear surface 36, the legs 63 and the through holes 89 are all perpendicular to the horizontal plane formed between the passages 84 (more than merely perpendicular to the jig longitudinal axis II-II).

In the construction shown in FIG. 3A, the positioning block 82 includes two fixation through holes 85 extending from the front surface to the rear surface of the positioning block 82 for receiving two pins to provide optional fixation of the jig 80 on distal femur. The number of the fixation through holes may be increased or reduced as desired, and the axes of the fixation through holes may be or may not be parallel with the jig longitudinal axis II-II, as long as pins may be passed through those fixation through holes and fixed the jig 80 onto the distal femur.

The positioning block 82 shown in the embodiment of FIG. 3A also comprises two optional stop plates 86 protruding respectively from its upper and lower surfaces at the distal end of the positioning block 82 and each having a recess 88 formed at a central portion. The stop plates are used for abutting against on the end face of the distal femur. As mentioned above, the distal end face of the positioning block 82 per se can be used for abutting against the end face of the distal femur, and the two stop plates 86 may be omitted. The recess 88 of each stop plate 86 has a shape conforming to the bottom shape of the base portion 65 of the distal femoral jig outrigger 60. Furthermore, since the distal femoral jig is for medical use, preferably, the left and right sides of the positioning block 82 are rounded to avoid injury or trauma. More preferably, the stop plates 86 and the left and right sides of the positioning block 82 are all rounded to avoid injury or trauma.

Due to the at least one vertical through hole of the distal femoral jig 80, the at least one vertical leg of the distal femoral jig outrigger 60 can be inserted into the distal femoral jig 80 from both sides, allowing the apparatus to flip round (see FIGS. 6, 7A and 7B). Due to such a flip feature, the cutting apparatus can be adapted to both left leg and right leg with a simple structure and simplified operation. In particular, the distal femoral jig 80 comprises two flip orientations: in the first flip orientation (as shown in FIG. 7A) the rod 21 can be inserted in a selected one of the at least one passage having a preset valgus angle for one of the left and right legs, and when the distal femoral jig 80 is flipped over about 180° about its axis (best shown in FIG. 6) to the second flip orientation (as shown in FIG. 7A) the rod 21 can be inserted similarly alternatively in a selected one of the at least one passage having a preset valgus angle for the other one of the left and right legs. In the embodiment of FIG. 7A and FIG. 7B for a patient with about symmetrical skeletal anatomy having the same valgus angle (on the opposite sides of the anatomical axis) for both the left leg and the right leg, inserting the rod 21 into a passage before flipping the distal femoral jig fits a first leg (e.g. left leg) and after flipping inserting the rod 21 into the same passage fits the other leg (e.g. right leg) at the same valgus angle (e.g., 7°). Thus, having two passages suitable for use with flipping adaptation for two preset valgus angles (such as 5° and 7°) the distal femoral jig provides for flexibility of having two valgus angles to select from for both the left leg and the right leg. More than two passages might be used.

Figures 5A, 5B:
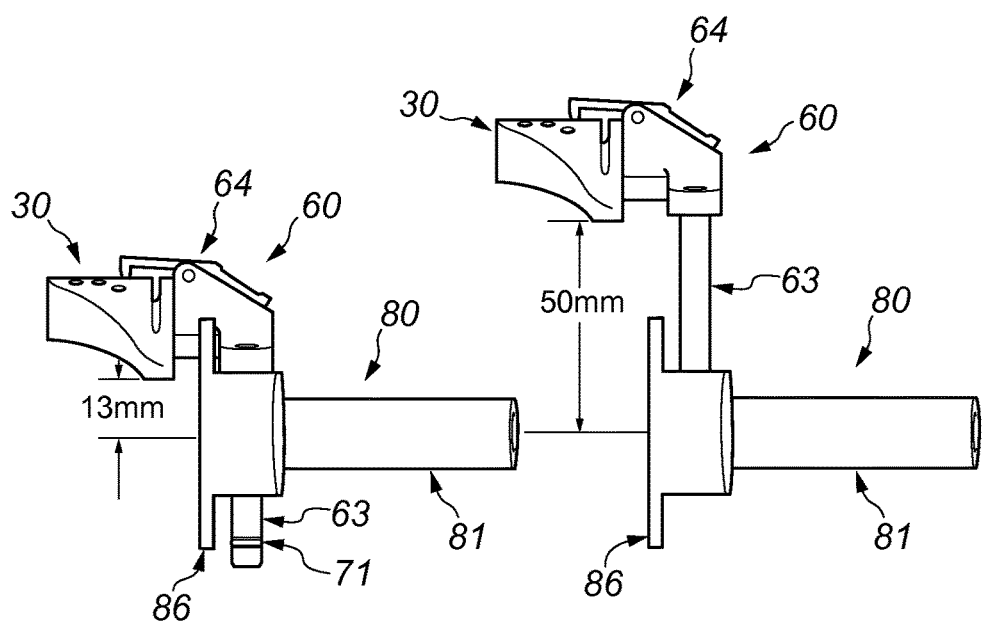
FIG. 5A and FIG. 5B are side views of the assembled distal femoral cutting block and the distal femoral jig assembly shown in FIG. 4 with different heights.

When the at least one leg 63 of the jig outrigger 60 is inserted into the respective at least one through hole 89 of the jig 80, the trunion 69 of the jig outrigger 60 is inserted into the central opening 37 of the cutting block 30, and the tip end 68 bites into the central hole 34, the cutting block 30, jig outrigger 60 and jig 80 are assembled together. Due to the leg and hole assembling manner of the at least one leg 63 of the jig outrigger 60 and the at least one through hole 69 of the jig 80, the cutting block 30, jig outrigger 60 and jig 80 can be assembled/disassembled quickly and easily. In addition, also due to the leg and hole assembling manner, the apparatus may be adjusted to different femurs having much different sizes. When in use, the distal femoral cutting block 30 will be positioned on the distal femur of the patient and the distal end face of the distal femoral jig 80 will abut against the end face of the distal femur. Taking the distance between the substantially flat lower surface portion 39 of the cutting block 30 and the longitudinal axis II-II of the distal femoral jig 80 as a measure, the cutting block can be adjusted from a minimum of 13 mm at the lowest point as shown in FIG. 5A and a maximum of 50 mm at the highest point as shown in FIG. 5B. At the lowest point, the base portion 65 of the outrigger 60 is positioned in the recess 88 of the stop plate 86 and the distal face of the beam 62 abut against the stop plate 86. At the highest point, the C-clip 71 provides friction to prevent the outrigger 60 from sliding off the jig 80. So the cutting apparatus according to the present invention can be applied on much different patients.

All of the elements of the cutting apparatus are formed by medical use materials, such as medical grade stainless steel, a nickel-titanium based alloy such as Nitinol, and the like. The cutting apparatus is provided non-sterile and stored in a sterilization case. It can be sterilized using an approved sterilization method as stated in the appropriate instructions for use (IFU) document.

FIGS. 8A to 15 show the operation of the cutting apparatus according to the present invention.

With the patient's knee in flexion, a surgeon may remove osteophytes from the intercondylar notch to clear the position. Since correct location of the medullary canal is critical to avoid malposition of the femoral component, the following procedure must be implemented carefully to avoid the cortices. The surgeon firstly positions a drill to enter the medulary canal slightly superior and medial to the midline of the trochlea, 7 mm to 10 mm anterior to the origin of the posterior cruciate ligament (see FIG. 8A). In the proper position, the drill should pass easily into the femoral canal.

Figure 8A:
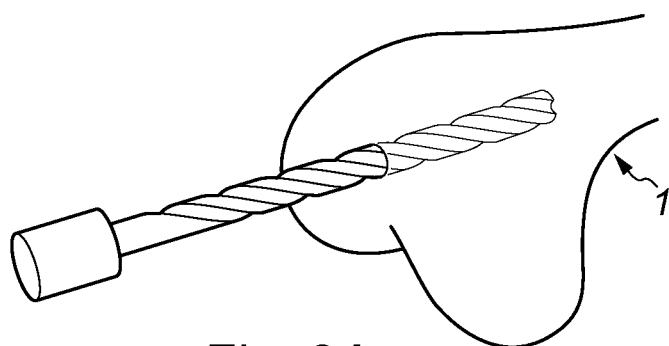
FIG. 8A is a view showing a drill drilling a hole in a distal femur and FIG. 8B is a view showing the drill enlarging the hole in the distal femur.
Figures 8B, 9:
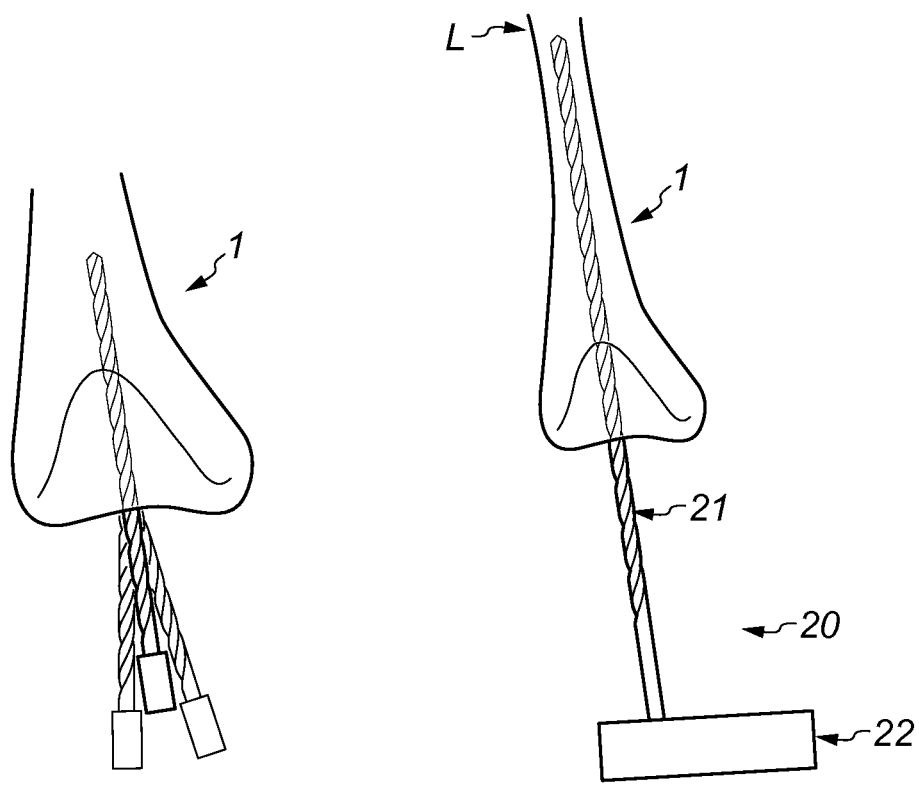
FIG. 9 is a view showing a rod with a handle of the distal femoral cutting apparatus is inserted into the hole formed in the distal femur of FIG. 8A and/or FIG. 8B.
Figure 10:
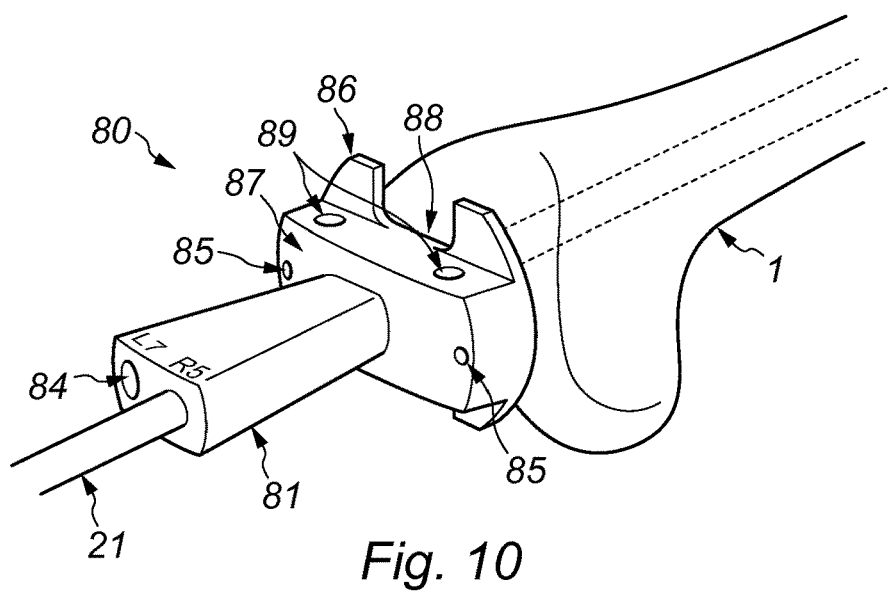
FIG. 10 is a view showing the distal femoral jig sliding on the rod and abutting against a distal face of the distal femur.

The diameter of the hole drilled in the distal femur could be increased if required (see FIG. 8B). This will allow depressurization of the canal when the rod is inserted.

When a desired hole is drilled in the knee, the surgeon introduces slowly the rod 21 of the rod assembly 20 into the medullary canal to the level of the isthmus L (see FIG. 9). As mentioned above, the rod 21 aids to relieve intramedullary pressure. The rod assembly 20 is subsequently withdrawn. Please note that although the above procedure illustrates the Femur First technique, the present technique can also be performed using the Tibia First approach.

The surgeon may use preoperative radiographs to define the angle between the femoral anatomical and mechanical axes. According to the specific dimension of the knee of the patient, the surgeon may select the appropriate valgus angle (for example, left or right: 5° or 7°) (FIGS. 7A and 7B) of the distal femoral jig by sliding the jig 80 onto the rod 21 towards the femur until the distal end face of the jig or the stop plates 86 of the jig contact the end face of the distal femur (see FIG. 10). If the surgeon worries about the positioning of the distal femoral jig 80, pins may be inserted into the fixation holes 85 to fix the jig 80 to the distal femur.

The surgeon may then assemble the distal femoral cutting block 30 to the distal femoral jig outrigger 60 by inserting the trunion 69 into the central opening 37 and simultaneously pressing the button 70 of the outrigger 60 (see FIG. 11) to let the tip end 68 bite into the central hole 34. After that, the surgeon can put the assembled cutting block 30 and the outrigger 60 above the distal femoral jig 80 and position the at least one leg 63 into the at least one hole 89 of the jig 80 until the cutting block 30 touches the anterior femur (see FIG. 12). Then the apparatus is in a state as shown in FIG. 1 or 2A.

Figure 13:
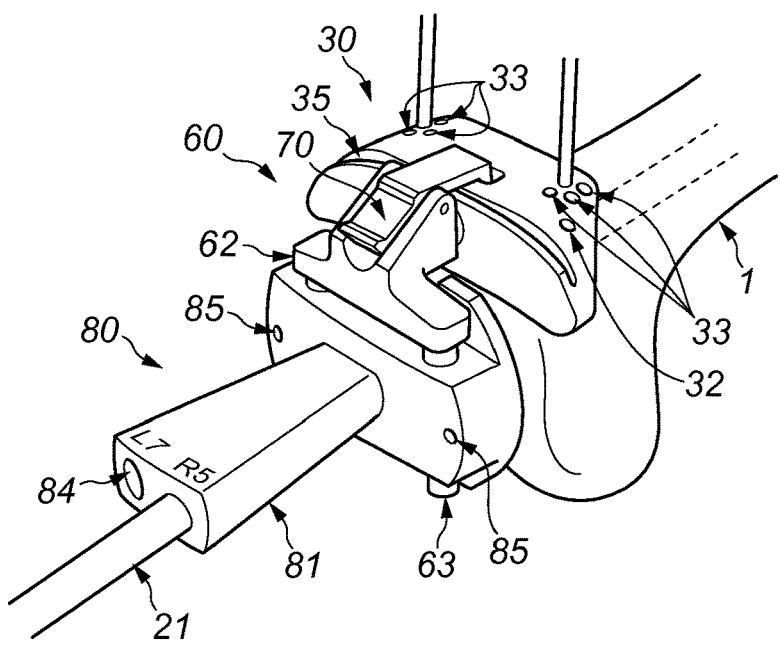
FIG. 13 is a view showing that the distal femoral cutting apparatus is affixed to the distal femur by fasteners.

When the surgeon opines that the cutting block 30 is properly positioned, he or she may insert two pins (such as Steinmann pins) through the reposition holes 33 marked with "0" into the posterior condyles to fix the cutting block 30 onto the distal femur, as shown in FIG. 13.

Figure 14:
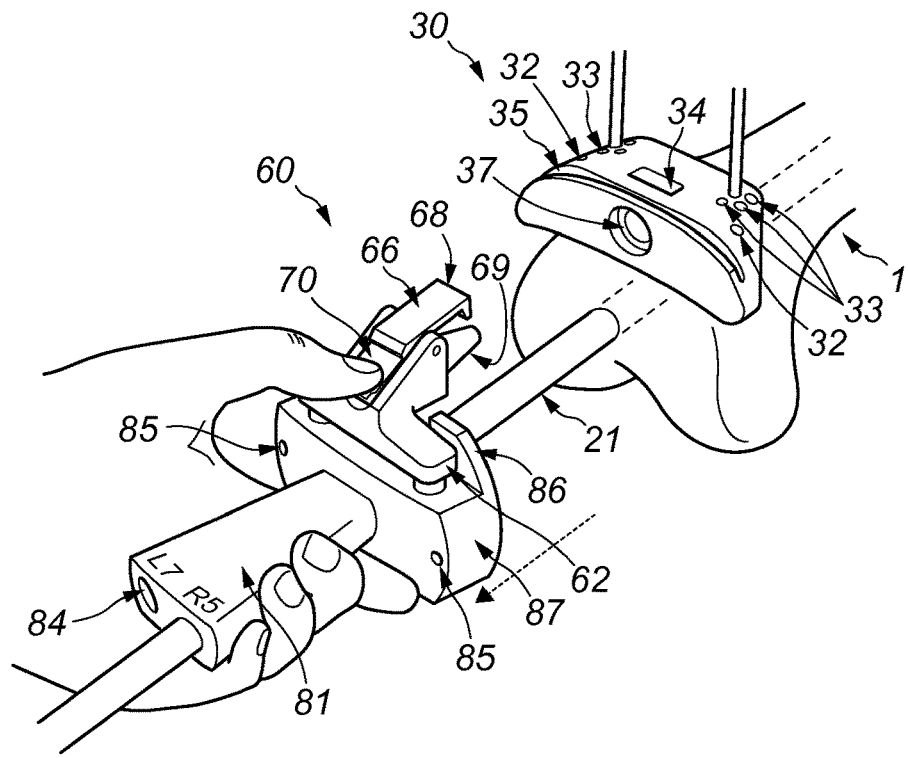
FIG. 14 is a view showing that the distal femoral jig assembly is disengaged with the distal femoral cutting block.
Figure 15:
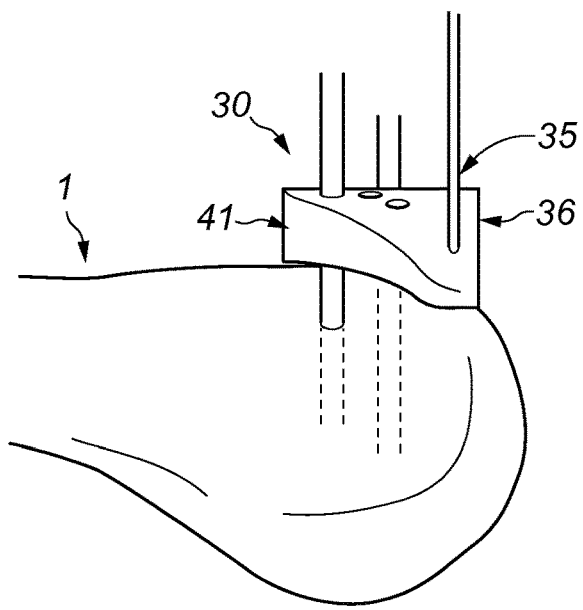
FIG. 15 is a view showing a saw blade extending through a cutting slot of the distal femoral cutting block to resect the distal femur.

The surgeon could appropriately arrange the cutting block 30 onto the distal femur by a series of adjusting motions. The surgeon may then push the button 70 using his thumb to release the tip end 68 from the central hole 34 so that the distal femoral jig assembly 50 is released from the cutting block 30. The surgeon may withdraw the jig assembly with one hand as shown in FIG. 14.

Of course, even at this step, the surgeon still has a chance to adjust the position of the cutting block 30 due to the reposition holes 33. To further adjust the distal resection depth once the distal femoral jig assembly 50 is removed, the surgeon may use the distal or proximal reposition holes 33, which move the cutting block (for example, 2 mm in the device shown in the drawings) in distal direction or (for example, 2 mm or 4 mm in the device shown in the drawings) in proximal direction (FIG. 13). Furthermore, if it is necessary for additional stability, the surgeon may insert one or more pins (for example Steinmann pins) through one or more of the convergent pin holes 32 on the cutting block 30.

The cutting block 30 is left on the distal femur. Now the surgeon may use a saw blade to resect the distal face of the femur via the cutting block 30. As described above, the cutting block 30 is formed with one or more (or say at least one) cutting slots 35. The saw blade may be inserted into one of the cutting slots 35 to resect corresponding depth of the femur (see FIG. 15). Alternatively, the surgeon may initiate the resection from the proximal end face 36 of the cutting block 30, which is parallel with the cutting slots and this will resect 4 mm less distal femur.

The surgeon may remove the pin from the convergent pin hole 32 and the distal femoral cutting block 30 once the resection has been completed. If further resection is needed, the surgeon may leave the fixation pins in place for refining the distal femoral cut by adjustment the position of the distal femoral cutting block 30.

The fixation pins are also removed once the resection is finished.

The invention claimed is:

1. A distal femoral jig assembly used with a cutting apparatus for resecting a distal face of a femur prior to implanting a femoral component of a total knee prosthesis, the cutting apparatus comprising:
   (i) a rod adapted for inserting into an intramedullary canal of the femur, and
   (ii) a distal femoral cutting block configured for guiding resection of the distal face of the femur,
   in which the distal femoral jig assembly is capable of positioning the distal femoral cutting block on either a left leg or a right leg and comprises a distal femoral jig and a distal femoral jig outrigger having at least one vertical leg, the distal femoral jig comprising:
   (a) a positioning block having a distal end face which is adapted for abutting against the distal face of the femur, and at least one vertical through hole extending through it from an upper surface to an opposite lower surface thereof, the through hole being configured to receive the vertical leg on the outrigger, and
   (b) a guiding bar which is formed integrally with the positioning block and extends proximally from the positioning block, the guiding bar extending along a longitudinal axis of the jig which extends perpendicular to the distal end face of the positioning block,
   in which first and second passages extend through the guiding bar and the positioning block, in a convergent manner in a direction towards the patient's femur when the jig is in use, the first and second passages each being configured for slidingly receiving the rod with respective first and second preset valgus angles, and
   in which the distal end face of the positioning block can abut against on the distal face of the femur of either the left leg or the right leg dependent on two flip orientations in which, in a first flip orientation the rod can be inserted in a selected one of the first and second passages having an appropriate preset valgus angle for one of the left and right legs, and in a second flip orientation after the distal femoral jig being flipped over approximately 180° about a jig longitudinal axis the rod can be inserted in a selected one of the first and second passages having the appropriate preset valgus angle for the other one of the left and right legs.

2. The distal femoral jig assembly according to claim 1, in which the distal femoral jig is adapted to allow the rod to be inserted in the selected one of the first and second passages, resulting in the valgus angle for the left leg and the right leg being the same by flipping over the distal femoral jig.

3. The distal femoral jig assembly according to claim 1, in which a valgus angle difference between the two passages is 1° to 3° and the two valgus angles both are between 4° and 10°.

4. The distal femoral jig assembly according to claim 3, in which the two passages are adapted for receiving the rod for sectioning the femur corresponding to a 5° valgus angle and a 7° valgus angle.

5. The distal femoral jig assembly according to claim 1, in which the positioning block comprises two stop plates protruding from the upper surface and the lower surface and at a distal end of the positioning block.

6. The distal femoral jig assembly according to claim 1, in which the distal femoral jig outrigger has a support having a beam and the at least one leg extending from the beam vertically and downwardly and a clip arranged on the beam, the clip having a hook-like tip end for biting into a central hole formed in the upper surface of the distal femoral cutting block.

7. The distal femoral jig assembly according to claim 6, in which at least one leg of the at least one leg of the distal femoral jig outrigger has a groove formed circumferentially around its lower end and a C-clip is arranged in the groove for providing friction to prevent the distal femoral jig outrigger from sliding off the distal femoral jig.

8. The distal femoral jig assembly according to claim 6, in which the distal femoral jig outrigger further comprises a trunnion extending distally from the beam for inserting into a central opening formed in the proximal surface of the distal femoral cutting block.

9. The distal femoral jig assembly according to claim 8, in which the trunnion comprises a substantially cylindrical portion and a truncated cone portion having a largest diameter smaller than a diameter of the cylindrical portion, the central opening of the distal femoral cutting block is a tapered counterbore having a stepped portion.

10. The distal femoral jig assembly according to claim 9, in which the positioning block comprises two stop plates protruding from the upper surface and the lower surface and at a distal end of the positioning block and in which each stop plate has a central recess conforming to a bottom shape of a base portion of the trunnion.

11. The distal femoral jig assembly according to claim 10, in which the guiding bar has a tapered shape or a cone shape.

12. The distal femoral jig assembly according to claim 10, in which the positioning block includes at least one fixation hole extending through the positioning block from a proximal surface to a distal surface.

13. A cutting apparatus for resecting a distal face of a femur prior to implanting a femoral component of a total knee prosthesis, comprising:
   (a) a distal femoral jig assembly as claimed in claim 1,
   (b) an elongate rod adapted for inserting into an intramedullary canal of the femur, and
   (c) a distal femoral cutting block configured for guiding resection of the distal face of the femur.

14. The cutting apparatus according to claim 13, in which a handle is removably attached to, or formed integrally with, a proximal end of the rod for withdrawing the cutting apparatus.

15. The cutting apparatus according to claim 13, in which the distal femoral cutting block comprises at least one slot for selectively cutting off different lengths of the distal femur.

* * * * *